(12) United States Patent
Ohmer et al.

(10) Patent No.: US 11,166,669 B2
(45) Date of Patent: *Nov. 9, 2021

(54) METHOD FOR DETERMINING OF MOVEMENT PATTERNS DURING A DENTAL TREATMENT

(71) Applicant: Valutis GmbH, Herxheim (DE)

(72) Inventors: Benjamin Ohmer, Munich (DE); Stefan Raith, Mitterfels (DE)

(73) Assignee: VALUTIS GMBH, Herxheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/076,129

(22) Filed: Oct. 21, 2020

(65) Prior Publication Data

US 2021/0030352 A1 Feb. 4, 2021

Related U.S. Application Data

(63) Continuation of application No. 16/694,550, filed on Nov. 25, 2019, now Pat. No. 10,813,587, which is a (Continued)

(30) Foreign Application Priority Data

Jun. 19, 2013 (DE) ...................... 10 2013 010 292.8
Sep. 18, 2013 (DE) ...................... 10 2013 015 537.1
Dec. 17, 2013 (DE) ...................... 10 2013 021 492.0

(51) Int. Cl.
*A61B 5/00* (2006.01)
*A46B 15/00* (2006.01)
(Continued)

(52) U.S. Cl.
CPC .......... *A61B 5/486* (2013.01); *A46B 15/0006* (2013.01); *A46B 15/0012* (2013.01);
(Continued)

(58) Field of Classification Search
CPC ..... A61B 5/486; A61B 5/1123; A61B 5/1128; A61B 5/0077; A61B 5/4833;
(Continued)

(56) References Cited

U.S. PATENT DOCUMENTS 6,536,068 B1 3/2003 Yang et al.
6,786,732 B2 9/2004 Savill et al.
(Continued)

FOREIGN PATENT DOCUMENTS

CN 102215922 A 10/2011
DE 10045067 A1 4/2002
(Continued)

OTHER PUBLICATIONS

Examination report from the Indian Patent Office dated Dec. 23, 2019 in related IN application No. 201617001306.
(Continued)

*Primary Examiner* — An H Do
(74) *Attorney, Agent, or Firm* — J-TEK Law PLLC; Jeffrey D. Tekanic; Scott T. Wakeman

(57) ABSTRACT

An electric toothbrush includes a brush head at an end of a handle, an acceleration sensor and/or a rotation sensor that detect(s) movement parameters of the electric toothbrush, a wireless communication interface that wirelessly transmits recorded data comprising the detected movements parameters of the electric toothbrush in a processed state and receives treatment mode data for operating the electric toothbrush, a pressure sensor that detects a contact pressure applied by the brush head to teeth and/or gums, at least one first outputting device that visually outputs signals or commands in accordance with the detected contact pressure or in accordance with the detected movement parameters, and at least one second outputting device that haptically outputs signals or commands, in the form of vibrations, in accor-
(Continued)

dance with the detected contact pressure or in accordance with the detected movement parameters.

31 Claims, 2 Drawing Sheets

Related U.S. Application Data continuation of application No. 16/210,111, filed on Dec. 5, 2018, now Pat. No. 10,517,532, which is a continuation of application No. 14/898,176, filed as application No. PCT/EP2014/062077 on Jun. 11, 2014, now Pat. No. 10,172,552.

(51) Int. Cl.
    *A61C 17/22*     (2006.01)
    *A61B 5/11*     (2006.01)
    *A61C 19/04*     (2006.01)

(52) U.S. Cl.
    CPC .......... *A61B 5/0077* (2013.01); *A61B 5/1123* (2013.01); *A61B 5/1128* (2013.01); *A61B 5/6898* (2013.01); *A61C 17/221* (2013.01); *A61C 19/04* (2013.01); *A46B 2200/1066* (2013.01); *A61B 5/4833* (2013.01); *A61C 17/22* (2013.01)

(58) Field of Classification Search
    CPC ... A61B 5/4547; A46B 15/0006; A46B 13/02; A46B 15/0016; A46B 9/04; A46B 2200/1066; A61C 17/22; A46D 99/00
    USPC .............................................. 702/85, 94, 95
    See application file for complete search history.

(56) References Cited

U.S. PATENT DOCUMENTS

| | | | |
|---|---|---|---|
| 7,748,069 B2 | 7/2010 | Dawley | |
| 9,498,053 B2 | 11/2016 | Patel et al. | |
| 9,642,685 B2 | 5/2017 | Brodkin et al. | |
| 9,724,001 B2 | 8/2017 | Dykes et al. | |
| 9,757,065 B1 | 9/2017 | Suri et al. | |
| 9,882,986 B2 | 1/2018 | Patel et al. | |
| 9,901,256 B2 | 2/2018 | Seibel et al. | |
| 9,907,463 B2 | 3/2018 | Elazar et al. | |
| 9,918,013 B2 | 3/2018 | Ryan et al. | |
| 9,950,434 B2 | 4/2018 | Binder et al. | |
| 10,172,552 B2 | 1/2019 | Ohmer et al. | |
| 10,517,532 B2 | 12/2019 | Ohmer et al. | |
| 10,813,587 B2 | 10/2020 | Ohmer et al. | |
| 2002/0183959 A1 | 12/2002 | Savill et al. | |
| 2005/0070782 A1 | 3/2005 | Brodkin | |
| 2008/0146887 A1 | 6/2008 | Rao et al. | |
| 2009/0092955 A1 | 4/2009 | Hwang | |
| 2009/0130636 A1 | 5/2009 | Hwang | |
| 2009/0215015 A1 | 8/2009 | Chu | |
| 2010/0170052 A1 | 7/2010 | Ortins et al. | |
| 2010/0281636 A1 | 11/2010 | Ortins et al. | |
| 2010/0323337 A1 | 12/2010 | Ikkink et al. | |
| 2011/0010876 A1 | 1/2011 | Iwahori et al. | |
| 2011/0131014 A1 | 6/2011 | Bates et al. | |
| 2011/0247156 A1 | 10/2011 | Schmid et al. | |
| 2011/0275424 A1 | 11/2011 | Schmid et al. | |
| 2012/0251975 A1 | 10/2012 | Iwahori | |
| 2012/0295218 A1 | 11/2012 | Moll | |
| 2012/0317817 A1 | 12/2012 | Binder | |
| 2013/0091642 A1 | 4/2013 | Dykes et al. | |
| 2013/0151662 A1 | 6/2013 | Patel | |
| 2013/0323674 A1 | 12/2013 | Hakomori et al. | |
| 2014/0065588 A1 | 3/2014 | Jacobson et al. | |
| 2014/0215370 A1 | 7/2014 | Berry | |
| 2015/0381923 A1 | 12/2015 | Wickenkamp et al. | |
| 2016/0143718 A1 | 5/2016 | Serval et al. | |
| 2016/0284208 A1 | 9/2016 | Pfenniger et al. | |
| 2016/0296163 A1 | 10/2016 | Chaudhry et al. | |
| 2017/0079421 A1 | 3/2017 | Tamminga et al. | |

FOREIGN PATENT DOCUMENTS

| | | |
|---|---|---|
| DE | 10154946 A1 | 5/2003 |
| DE | 102008027317 B4 | 11/2011 |
| DE | 102011103301 A1 | 12/2012 |
| EP | 2384720 | 11/2011 |
| WO | 2006137648 A1 | 12/2006 |
| WO | 2011073010 A1 | 6/2011 |
| WO | 2014036423 A1 | 3/2014 |

OTHER PUBLICATIONS

Flagg et al., "An Intelligent Toothbrush: Machines for Smart Brushing," pp. 1-4, Jun. 2011, Department of Occupational Science and Occupational Therapy, University of Toronto.

Christian Peters, et al., "User Behavior Recognition for an Automatic Prompting System—A Structured Approach based on Task Analysis", Proceedings of the 1st International Conference on Pattern Recognition Applications and Methods—vol. 1: ICPRAM, ISBN 978-989-8425-99-7 ISSN 2184-4313, pp. 162-171. DOI 10.5220/0003773601620171.

Young-Jae Lee, et al., "Toothbrushing Region Detection Using Three-Axis Accelerometer and Magnetic Sensor"; IEEE Transactions on Biomedical Engineering, vol. 59, No. 3, Mar. 2012, pp. 872-881.

METHOD FOR DETERMINING OF MOVEMENT PATTERNS DURING A DENTAL TREATMENT

CROSS-REFERENCE

This application is a continuation of U.S. patent application Ser. No. 16/694,550, now pending, which is a continuation of U.S. patent application Ser. No. 16/210,111, now U.S. Pat. No. 10,517,532, which is a continuation of U.S. patent application Ser. No. 14/898,176, now U.S. Pat. No. 10,172,552, which is the US national stage of International Patent Application No. PCT/EP2014/062077 filed on Jun. 11, 2014, which claims priority to German Patent Application No. 10 2013 010 292.8 filed on Jun. 19, 2013, German Patent Application No. 10 2013 015 537.1 filed on Sep. 18, 2013 and German Patent Application No. 10 2013 021 492.0 filed on Dec. 17, 2013.

TECHNICAL FIELD

The invention generally relates to systems and methods for determining movement patterns during a dental treatment, such as a teeth cleaning.

RELATED ART

Due to relatively large intervals of time (e.g., several months or even years) between dental visits, a problem results in that the instructions of the dentist with respect to frequency, duration and manner of treatment (e.g., cleaning) are easily forgotten, or over time non-optimal motion sequences (e.g., brushing movements or brush strokes) establish (become habitual), whereby oral hygiene is not optimally ensured and/or deterioration of the oral cavity, in particular of solid and/or soft oral parts, like e.g. the teeth, the jaw and/or the gum, is caused.

To address this problem, European patent publication EP 1 379 149 B1 discloses a method for monitoring the position of a toothbrush with respect to the teeth of a person, which comprises: providing a toothbrush with a first position sensor, wherein the first position sensor sensitively reacts to changes of the position and orientation of the toothbrush, providing a second position sensor in a fixed positional relationship with respect to the teeth, wherein the second position sensor sensitively reacts to changes of the position and orientation of the teeth, and transmitting the outputs of the first position sensor and the second position sensor to a processing apparatus, so that the processing apparatus compares both sensor outputs in order to monitor the position of the toothbrush with respect to the teeth during the tooth brushing.

However, this known system is disadvantageous, since expensive sensors must be attached to the face in a defined manner, which makes the system costly and complex, thereby making a high market acceptance market difficult.

In the article "Playful Toothbrush: UbiComp Technology for Teaching Tooth Brushing to Kindergarten Children", Yu-Chen Chang et. al. describe a system in which the movement of the toothbrush is optically detected. However, this system is disadvantageous, since the detected movements take place in an undefined manner in space, such that a movement of the head during the optical detection causes a corruption of the detected data. Furthermore, expensive modifications of the toothbrush are required, which makes the system complex and costly and thus it appears to be unlikely to achieve mass market acceptance. Additionally, it is problematic that the system has to be installed in a fixed manner in space, so that a camera can detect the modified toothbrush in a defined manner.

Further, both of the above-described known systems are based on given (predetermined) data sets, such that an enhancement of the knowledge with respect to tooth brushing movements is not possible.

SUMMARY

Therefore, in one non-limiting aspect of the present teachings, methods and systems are disclosed, which facilitate an optimization of oral health, such as oral hygiene, tooth health, jaw health and/or gum health. In addition or in the alternative, the present teachings also facilitate a control, such as continuous or permanent control, or a monitoring, such as continuous or permanent monitoring, of the oral hygiene. In addition or in the alternative, the present teachings provide simple, low-priced and widely-usable methods and devices.

A method according to another aspect of the present teachings preferably comprises: (i) moving a dental treatment means at least in an X/Y plane in order to treat surface portions of the teeth, (ii) capturing (recording) data relating to at least one movement parameter, such as the movement direction or rotation, the acceleration, the path and/or the speed, of the dental treatment means relative to a first reference system that moves with the head of the treated person using at least one optical detection device, (iii) defining a second three-dimensional reference system using a processor device based on characteristic body points of the hand, body lines of the hand and/or body surfaces of the hand that is guiding (moving) the dental treatment means, wherein the second reference system moves at least at times (preferably constantly) during movement of the dental treatment means in space with the dental treatment means, (iv) providing the recorded data to a processor device for determination of the movement pattern and (v) determining the movement pattern.

Preferably, the dental treatment means is moved at least at times in a three dimensional manner, i.e. in the X-, Y-, and Z-directions, and the movement parameters are particular preferably dependent on the direction and/or orientation recorded (captured). The X-Y plane extends in the X-direction and in the Y-direction, possible other planes extend in an analogous manner, and the X-axis, Y-axis and Z-axis are orthogonal to each other.

Alternatively or additionally, a method of at least partially determining a movement pattern of the dental treatment means (e.g., a toothbrush) during the dental treatment (e.g., a teeth cleaning), preferably in an individual-related (personalized) manner, according to another aspect of the present teachings preferably comprises at least (i) optical recording (capturing) of data, such as by using at least one camera, with respect to at least one movement parameter, such as the movement direction or rotation, the acceleration, the traveled path and/or the speed, of the dental treatment means, (ii) image separation of the dental treatment means, such as of the hand guiding the dental treatment means, from at least one further image part recorded (captured) using the optical detection device and (iii) determining at least one movement parameter corresponding to the movement pattern.

Such embodiments are advantageous, since the data recording (capture) can take place anywhere and at any time and thus a monitoring and objective evaluation of the dental treatment can take place also at the homes of private individuals at any time, i.e. in a time-independent manner.

The recorded (captured) data are to be processed, e.g., in real time, in such a manner, or are preferably processed in real time in such a manner, that the movement pattern is analyzable by e.g. an attending dentist or a private individual or a patient, whereby individualized (customized) adaptations (adjustments) of the movement patterns can immediately be made during a dental treatment. The data collected in such a manner can be used not only individually for acute (immediate) optimization of the movement pattern, but can also be used in larger scale, e.g., by health insurance companies and/or research institutes. By transferring data collected from multiple users to a central evaluation station, on the one hand, it opens up the possibility, e.g., to process the raw data in a centralized manner with adequate computing power, to compare it with optimal movement schematas and to send it to the local end-user devices; on the other hand, it is additionally or alternatively possible to provide data for large clinical studies for research purposes or for commercial statistical usage (e.g. by health insurance companies).

According to a further embodiment of the present teachings, a method for determining at least one movement characteristic preferably comprises at least: (i) carrying out one of the above-described methods multiple times, such as on different end-user devices for recording (capturing) movement patterns of different persons and preferably the statistical evaluation thereof, wherein it is additionally or alternatively also conceivable that a movement characteristic is generated or determined for one person, and (ii) determining at least one coinciding property, such as a movement parameter and/or the dental treatment duration, of the determined movement patterns or the recorded data.

This embodiment is advantageous, since one or more movement characteristics are derivable from the movement pattern of individual persons, which movement characteristics are representative of the dental treatment behavior of the respective person. However, it is additionally or alternatively conceivable that the movement patterns or movement characteristics of individual persons are to be grouped or are grouped based on coinciding features. Furthermore, the determined movement patterns or the recorded data may be correlated with characteristic standard data, which are provided in a database, wherein the database is at least partially provided (stored) locally on a mobile end-user device and/or at least partially on a server.

Furthermore, during usage of the device, it is possible to provide a step of outputting (e.g., optical, haptic and/or acoustic outputting) information concerning correction-, standard- and/or ideal-movements, such as in accordance with the currently-, i.e. e.g. in real time, determined movement patterns or in accordance with an already determined movement pattern or a movement characteristic. Optical outputting herein preferably means the visual depiction (display) of correction-, standard- and/or ideal-movements on a screen or a projection surface, wherein visual outputting can be understood as the depiction (display) of individual images and/or an animated movie. Acoustic outputting herein preferably means the outputting of specific tones and/or the outputting of spoken instructions. Haptic outputting can be understood e.g. as a defined output of vibrations. In particular with respect to the optical outputting, the correction-, standard-, and/or ideal-movements preferably can be output adjacent, over and/or in correlation to the actually recorded (captured) movement patterns or to the actually recorded (captured) movement characteristics. Correction movements can herein include, e.g., the display of a suggestion for a movement change or adjustment as compared to the recorded (captured) movement pattern. Standard movements can be e.g. the average movements of a defined group of persons or those movements known from clinical studies. Ideal movements can be e.g. movements which are very gentle, cleansing and/or time-efficient, etc.

According to a further embodiment of the present teachings, a method for monitoring dental treatment movements and for outputting correction parameters for adapting the dental treatment movements preferably comprises the above-described method of at least partially determining a movement pattern of the dental treatment means (e.g., a toothbrush) during a dental treatment (e.g., a teeth cleaning), and further includes: (i) moving the dental treatment means at least in an X-/Y-plane to treat surface parts of the teeth, wherein data with respect to at least one movement parameter of the dental treatment means (e.g., the movement direction or rotation, the acceleration, the path and/or the speed) are recorded (captured) by preferably using an optical detection device, such as a camera, and (ii) providing the recorded (captured) data to a processor device or a system for determination of the movement pattern and the steps of comparing the determined movement pattern with movement patterns stored in a database, deriving or determining of correction parameters, such as at least one movement direction, for adapting (changing) the movement of the dental treatment means in accordance with the compared movement patterns, and outputting information using an output device in accordance with the derived or determined correction parameters.

This method is advantageous, since it outputs feedback or correction information concerning the movement sequence preferably directly to a person performing a dental treatment, such as a teeth cleaning, or feedback or correction information concerning the movement sequence can be output (e.g., in real time) to a person performing the dental treatment, should they guide the dental treatment means with a movement that was assessed, e.g., by software, as being inappropriate or with a movement pattern that was assessed as being inappropriate.

This embodiment is beneficial since e.g. children can be taught (e.g., supervised) the appropriate movement patterns identified with regard to the motion sequences during the dental treatment, such as teeth cleaning. An optical outputting device, like e.g. a screen of a mobile phone, a watch, a bracelet, a game console or a tablet PC, can output an image or a video that visually displays or outputs to the child the preferably optimal movement pattern, such as the movement patterns stored electronically in a local storage means and/or on a server and/or in a local or internet based database.

By using an optical detection device or optical capturing device, such as a camera, which is preferably in signal communication with the outputting device and which is preferably arranged in the same housing as the outputting device, the motions of the child are detectable and thus can be monitored. In case the child deviates from the displayed motions or movement patterns, then a signal is preferably output that clearly shows the deviation to the child. The detection device and the outputting device, such as for visual and/or haptic and/or acoustic outputting of signals and/or commands, are preferably components of a single apparatus, such as a mobile apparatus. The apparatus is herein preferably configured as a portable processor device, such as a mobile phone or tablet PC.

According to a further embodiment of the present teachings, a registration of the teeth to be treated preferably takes place, wherein the registration comprises optical recording (capturing) using the detection device or a manual recording (inputting) using an input screen (user interface), wherein the number and/or the location and/or the orientation and/or defects of at least individual teeth are recorded, and wherein the derivation or determination of the correction parameters preferably takes into account the registered teeth. Herein the input screen (user interface) can be e.g. visualized by a display means of an end-user device, such as of the end-user device that also comprises the detection device. Preferably, the number of teeth present and/or which location and/or which orientation and/or which defects that individual, multiple or all teeth have can be specified by a person using an input device, which preferably can be a component of the display means.

As was noted above, the derivation or determination of the correction parameters preferably takes into account of the registered teeth. For this purpose, the registration of the teeth can be carried out e.g. using the detection device, which may be optical such as a camera; i.e. preferably at least one image of the dentition is captured, wherein the image is analyzed using software and e.g. the number, direction and/or location and/or defects of the teeth are captured. Thus, it is also possible to capture tooth spaces (gaps) in the dentition.

Additionally or as an alternative, the number, direction and/or location and/or defects of the teeth may be capturable (inputable) manually, such as by using an input screen (user interface). Additionally or alternatively, the angle feature and/or sealings and/or dental crowns and/or inlays or filings of a single or of multiple teeth are capturable, such as by using the optical detection device. The location of the teeth preferably describes the position of the teeth or which tooth is the particular tooth (e.g. incisors, canine, premolars, molars). Furthermore, it is conceivable that properties of the individual teeth or relations between the individual teeth are capturable.

Gum recession and/or discolorations and/or dental calculus and/or cracks and/or breakages and/or holes and/or dental calculus etc., are preferably understood as being capturable defects according to the present teachings.

Furthermore, a calibration step may preferably take place once, repeatedly or several times. Herein, the determination of concrete (specific) and/or personal properties of the body, such as the height or the distance of the head to the detection device or to a reference point or the height or the distance of a part of the head to the detection device or to a reference point, is preferably understood herein as being a calibration.

Particular preferably, multiple body-fixed points and/or surface points are captured by the optical detection device during the calibration, wherein preferably one or multiple anterior teeth and/or the contact region extending in the tooth length direction or the boundary region between the anterior teeth is captured. Herein, it preferably involves the central incisor teeth, such as of the upper jaw, wherein it is also conceivable that the central incisor teeth of the lower jaw are also or alternatively captured.

The detection of the position of the incisor teeth of the upper jaw and/or the boundary region between those incisor teeth is often possible when the upper lip is pulled up, which however can not always be ensured during tooth brushing. Nevertheless, the detection of the position of the incisor teeth and/or the boundary region between the incisor teeth in relation to further anthropometric points of the face surface, such as of the nose, cheeks and forehead region, wrinkles, such as forehead wrinkles, or pupils, provides a possibility for defining a highly precise coordinate system and/or reference system on the head of a person.

For clinical studies, this preferably should or can be referenced with established dental coordinate definitions like e.g. the "Frankfurter horizontal plan", the "Camperschen plane", or the occlusal plane.

Furthermore, a coordinate system defined in that way additionally can be coupled to exactly or at least one, two, three further body points or to multiple body points, such as the nose, the chin, the forehead, one ear or two ears, etc. This is beneficial since, on the one hand, the once defined coordinate system is always detectable independently of the position of the lips, whereby the position of the teeth is always known, and on the other hand the shape of the body part, e.g. the nose, is irrelevant. The soft tissue deformation that typically occurs during mouth opening should or can be compensated by a correction computation to further raise the accuracy of the method.

According to a further embodiment of the present teachings, the optical recording (capturing) of an object takes place such that at least the extension of the object in one dimension, i.e. in length and/or in width and/or in height and/or circumference, is known and the extension of the object in the known dimension or in the known dimensions is preferably used for the determination of the dimension parameters, to capture geometric relations, like e.g. the length of the path travelled by the dental treatment means during a dental treatment and/or the dimension of the teeth, such as of the visible parts of the teeth, etc. Herein, the object is preferably the person who is using the dental treatment means, wherein the known dimension of the person is preferably his/her height. Additionally or alternatively it is conceivable that the object is the dental treatment means, such as the tooth brush, wherein the known dimension of the toothbrush is preferably the length and/or the width and/or the height and/or the circumference.

Additionally or alternatively it is conceivable that the object is an element, the dimensions of which are substantially identical everywhere on earth, like e.g. a CD, DVD or credit card. Preferably, data with respect to the properties of the dental treatment means are recordable using an identification means (cf. later embodiments).

In another aspect of the present teachings, a sensor device, such as a pressure sensor, for detecting the contact pressure applied by the dental treatment means to the mouth or the teeth and/or the gum may be provided in or on the dental treatment means or for bringing into contact with the dental treatment means. Alternatively or additionally, the pressure detection may be performed by the optical detection device. In this case, a bending of the dental treatment means is captured and is evaluated in accordance with known strength values. The strength values thus can be stored or are storable in a database.

Furthermore, the dental treatment means may be directly identified or the packaging thereof (e.g. a bar code or QR-code) may be optically recorded (captured) and identified. The identification of the dental treatment means enables thereby, that the information belonging to the specific dental treatment means regarding its properties, such as the strength values, are automatically stored for a processor device or are retrieved. Furthermore, the information concerning the properties of the dental treatment means also may be made available or recordable or registerable manually in a database, such as of a mobile end-user device. Preferable the information concerning the properties are storable electronically either locally on the mobile end-user device or on a server.

Thus, according to a further embodiment of the present teachings, a determination of the pressure during tooth cleaning, such as tooth brushing, applied by a dental treatment means, such as a toothbrush, to the teeth or gum of the person performing the tooth cleaning takes place, wherein an optical detection of the dental treatment means, such as directly or indirectly, takes place using the optical detection device, wherein information are captured or image data is generated by the detection device image and a deformation, such as an elastic deformation, e.g., bending, of the dental treatment means is determined using the image information or the image data, and wherein the pressure is determined at least in accordance with the deformation of the dental treatment means and preferably in accordance with further data that contains properties of the dental treatment means.

Furthermore, a signal or information may be output via an output device in accordance with the determined pressure. Preferably the signal or information represents a guidance for the user of the dental treatment means, such as the person undergoing the dental treatment. The determination of the pressure or the output of the signals and/or information to be output in accordance with the pressure preferably takes place in real time. The output of the signals and/or information particular preferably takes place using an optical outputting device. The optical outputting device is preferably a component of the device, such as of the end-user device, to which the optical detection device also belongs. The signals and/or information concerning the pressure are particular preferably communicated simultaneously and/or via the same outputting device to the same person; the correction parameters for adapting the dental treatment motions are also thereby communicated to a person, such as the person undergoing and/or performing the dental treatment. The data concerning the properties of the dental treatment means can include material properties and/or strength values and/or dimensions and/or bending stiffness and/or brand and/or age and/or the number of usages, such as operating life, etc.

According to a further embodiment of the present teachings, at least three preferably predetermined points, such as surface points, of a body, such as of a head, of a person, such as with respect to which surface points the movement patterns are recorded, preferably can be recorded using the optical detection device, wherein preferably at least two points are connectable or are virtually connectable or imaginarily connectable with one line and at least a third point does not lie on said line, wherein the reference system is defined by the at least three recorded points and wherein movement of the dental treatment means is recorded with respect to this reference system or wherein at least three preferably predetermined points of the dental treatment means, such as a tooth brush, are recorded using the optical detection device, wherein at least two points are connectable with one line and at least a third point does not lie on said line, wherein the reference system is defined by the at least three recorded points and wherein a movement of the person, such as of the head, is recorded (captured) with respect to this further reference system.

According to a further embodiment of the present teachings, in accordance with a movement of the body, such as of the head, of the person with respect to which the movement patterns are recorded, different points of the body (e.g., of the head) of the person are recorded relative to the optical detection device for the definition of the reference system. This embodiment is beneficial since the head of the person does not have to be completely motionless during execution of the method, but can preferably move and nevertheless a precise detection of the movement pattern is possible. Should a surface point captured for defining the reference system not be capturable any more e.g. as a result of a head rotation by the person, another body fixed or head fixed point or a surface point or multiple body fixed or head fixed points or surface points are preferably captured already before said surface point can not be captured anymore, by means of which point(s) the reference system can be further maintained. For example, in addition to characteristic shapes, like e.g. the tip of the nose, color changes of the skin, such as a pigment disorder, pigmented nevus, scars, body decorations, such as tattoos, the cavity of the eye, the incisor teeth, such as of the upper jaw, as well as points of devices attached to the body, such as to the head, like e.g. clothes, caps, glasses, can be captured as the body fixed or head fixed points or the surface points.

According to a further embodiment of the present teachings, the processor device is a mobile end-user device (e.g. a mobile phone or tablet PC) that sends the recorded data via the internet to a server device for further processing and/or receives data via the internet for output using an outputting means, wherein the data comprises information concerning motion parameters of the dental treatment means.

Furthermore, a system for an at least partial determination or an at least partially indirect determination of a personal and preferably dynamic movement pattern of a dental treatment means (e.g., in particular a toothbrush), during a dental treatment is disclosed. Herein, a dynamic movement pattern is preferably understood as being a movement pattern, which is at least partially defined by velocity information and/or acceleration information of the dental treatment means with respect to a treatment area. The system preferably comprises at least one detection device, such as a sensor device or an optical detection device, for recording (capturing) of data with respect to at least one movement parameter, such as the movement direction, the acceleration, the traveled path and/or the velocity, of the dental treatment means and at least or exactly one data processing device for generating movement patterns based on the recorded data.

Herein, the data processing device is preferably a device that is at least temporarily connectable with the internet, such as a computer, a digital camera, a gaming console, a tablet PC, a laptop, a wristwatch (e.g. a smart watch), a television and/or a mobile phone. Furthermore, the data processing device may generate the movement patterns partially or fully.

Particular preferably, the data processing device transmits the fully or partially generated movement patterns to a server device, which preferably receives personal movement patterns of dental treatment means from a plurality of data processing devices. The data transmission can take place e.g. in accordance with an energy-, connection-, time-, data volume- and/or dental-treatment-repeating-criteria, wherein the dental-treatment-repeating-criteria preferably specify a specific number of dental treatments. The connection criteria preferably specify the type and/or quality of the internet connection, e.g. whether it is a mobile phone rate plan or a local network, like e.g. a WLAN. The energy criteria preferably specify the state of charge of an end-user devise powered, such as with electricity, by a battery.

This criteria dependent transmission of the partially or fully generated movement patterns is beneficial, since the computation of the movement patterns primarily can take place on the side of the data processing device, i.e. on the end-user device side, and thus the amount of data transfer between the individual end-user devices and the server device can be kept relatively small. This is further beneficial since the server device needs to have a significant smaller computing power in case it receives partially or fully prepared movement patterns and can process them. The server device preferably does not have to start with effecting or computing the complete generation of movement patterns from the raw data.

However, it is alternatively also conceivable that the data recorded by the detection device are transmitted to the server device for processing. Thereby, transmitting can take place immediately after the recording or in accordance with specific criteria. Herein, the criteria can be e.g. an energy-, connection-, time-, data volume-, and/or dental-treatment-repeating-criteria. The server device preferably can be considered in this situation as a data processing device that processes the recorded data; that means a data processing device is not necessarily required on the end-user side or in the area of the detection device. Nevertheless, a processor device, such as a mobile phone, is preferably provided that at least effects the transmission of data to the server device.

In a particular preferred embodiment, the server device has access to clinically gathered information with respect to the dental health status, the number of dental visits per year and/or the treatment history, the used dental treatment means, etc. of specific persons and connects this information with the recorded movement pattern of the particular person using that device. The recorded movement patterns of a specific person are preferably associated with the specific person by a personalization instance, like e.g. a name request, a password request, a phone number, an email address or a pseudonym. This embodiment is beneficial, since unique monitoring and supervision are performable using the data generated by the server device, which data include the dental treatment status, the number of dental visits per year and/or the treatment history and the recorded movement parameters or the movement patterns, and teachings for further improvement of the dental treatment technique are derivable.

A dental treatment means (e.g., a toothbrush, oral douche, gas transmitter, such as an air emitter, sand emitter, driller, ultrasonic cleaner, etc.) that preferably can be employed or utilized in a system according to the present teachings preferably comprises at least one physical structure, wherein a treatment device for at least indirect bringing into contact with a tooth surface and a contact region for holding the dental treatment means is arranged or attached on the physical structure, wherein a detection device, such as a position-, velocity-, acceleration- and/or rotation sensor, for detection of movement parameter(s) is, at least during usage of the dental treatment means, physically connected with the physical structure. Herein, it is conceivable that the detection device is coupled or coupleable with any dental treatment means. Furthermore, it is conceivable that the detection device is fixedly or permanently coupled with the electric toothbrush.

According to a further embodiment of the present teachings, the dental treatment means comprises a communication interface for transmitting the recorded data, such as in a raw state or in a processed state, to a data processing device, wherein the communication interface is particular preferably designed in such a way that the data is transmittable wirelessly.

According to a further embodiment of the present teachings, the system comprises a processor device, such as a mobile end-user device, like e.g. a mobile phone, that preferably comprises at least one optical detection device, such as a camera, for detecting (recording) data of at least one motion parameter, such as the movement direction or—rotation, the acceleration, the traveled path and/or the velocity of a dental treatment means, and a data processing device for image separation of the dental treatment means from at least one other image component recorded (captured) by the optical detection device and for the determination of at least one movement pattern corresponding to the motion parameter(s).

The optical detection device is preferably used in the system as a detection device for the at least partial determination of a personal movement pattern during a dental treatment, such as a teeth cleaning.

In case the detection device is preferably designed as an optical detection device or optical capturing (recording) device, the dental treatment means may have an optically-distinctive shape, which preferably corresponds to an axis of an abscissa or serves to further facilitate a three-dimensional recording of one specific motion parameter of the dental treatment means during usage of exactly or at least one camera.

However, additionally or alternatively the dental treatment means also may be equipped with one or multiple sensor devices. In this case, the data processing device uses the sensor data and the data of the optical detection device for the determination of the motion parameter.

Furthermore, the dental treatment means also may be equipped with one or multiple sensor devices, in case the processor device or the system comprises at least or exactly one, two or multiple cameras, such as 3 cameras. In this case the data processing device can utilize data of one, some or all of the cameras and/or of the sensors for the determination of the motion parameter.

According to a further embodiment of the present teachings, the optical detection device comprises at least one, such as exactly or at least two, cameras for three-dimensional recording (capturing) of the at least one motion parameter of a dental treatment means, wherein the processor device defines a three-dimensional coordinate system or reference system that moves with the dental treatment means together in space during movement of the dental treatment means. Hereby the coordinate- or reference system can be constituted (defined) by characteristic anthropometric body points, body lines and/or body surfaces of a body part of a person, such as the hand with which the dental treatment means is being guided. However it also can be constituted additionally by surface points, surface lines and/or surface areas of the dental treatment means. The second camera is preferably fixedly arranged in relation the first camera, so that a once-only calibration of the detection system can take place before utilization. It is preferably also conceivable that the at least two cameras are moveable with respect to each other. The at least two cameras are preferably at least, exactly or maximally 2, 3, 4, 5 or 6 cameras.

According to a further embodiment of the present teachings, the optical detection device records (detects) a part (portion) of the head or at least three points of the surface of the head or three body-fixed points, which move during a movement of the person, such as of the head, together with the person, such as with the head, and define (establish) a three-dimensional coordinate system or reference system in the recorded part of the head or by means of these points, wherein a movement of the dental treatment means is determined in accordance with the defined coordinate system of the head or a movement of the recorded part of the head is determined in accordance with the coordinate system of the dental treatment means. Herein it is conceivable that the coordinate system is directly associated with the dental treatment means, wherein it is additionally or alternatively also conceivable that the coordinate system is at least partially (preferably completely) defined by defined body surface parts, such as two or more knuckles of the hand constituting the linkage between the palm of the hand and the fingers.

This embodiment is beneficial since: (i) a movement of any dental treatment means, such as any customary toothbrush or electric toothbrush, is optically at least indirectly at least partially detectable at least by recording (detecting) the hand movement and (ii) optical detection devices, such as hand cameras, are very wide spread, whereby the invention is applicable for an extremely large number of persons.

Particular preferably the dental treatment means is identifiable and separable from the remaining image parts by the data processing device in such a way that its movements, in particular with respect to or relative to a reference or coordinate system fixed on the head or in the region of the head of the person, are recordable and particular preferable analyzable.

Furthermore, preferably at least or exactly one body part of a person is additionally identifiable and separable from the remaining image parts by the data processing device in such a manner that a motion parameter of the dental treatment means is determinable or computable with respect to the body part. The body part is preferably a part (portion) of the head, like e.g. forehead, eyebrows, eye hole, mouth, lips, ears, cheeks and/or chin; more preferably, it is one or multiple body-fixed, such as cranium fixed, parts, like e.g. forehead, chin and/or nose.

However, it is also conceivable that multiple body parts, like e.g. the eyes, the mouth and/or nose are recorded. It is thus conceivable that one or multiple photos of the user or the patient, such as from the head or the face of the user, are recorded and stored.

Individual body shapes, such as face-part-shapes or shapes of characteristic face features, are preferably manually or automatically recordable or definable or are registerable as reference points or reference surfaces, with respect to which one or multiple motion parameters of the dental treatment means are recorded. For example, one or two eyes, the nose, the mouth, one or two ears and/or one or two lips can be used or registered as the reference point(s).

Furthermore, additionally or alternatively, the eye brows or the eyes, such as the pupils, of a person can be recorded. One line or axis can be defined or set connecting the eyes or the pupils, such as the centers of the eyes or pupils. This line or axis can define a direction, such as the x-, y- or z-direction, of a coordinate system.

Furthermore, a second line or axis can be defined or set in the direction of extension of the nose, such as of the nasal bridge, of that person which preferably defines a second direction differing from the first direction, such as the x-, y- or z-direction, of the coordinate system. Preferably the first direction and the second direction are substantially or exactly oriented orthogonally to each other. A third direction preferably extends orthogonally with respect to a plane defined by the first and second direction.

The recording of a movement of the dental treatment means with respect to a coordinate system coupled with a movement of the head is extremely beneficial since the person carrying out the dental treatment can move his/her head and/or body without causing the recording (capturing) of the movement patterns to become unprecise or impossible.

Furthermore, the present teachings concern the usage of a position-, velocity- and/or acceleration sensor or a video tracking system for the determination of a movement pattern of a dental treatment means during a dental treatment.

In another aspect of the present teachings, a method is disclosed for at least partially determining of a pressure resulting during a dental treatment, such as a teeth cleaning, and applied by a dental treatment means to the teeth or the gum of a person undergoing the dental treatment. The method preferably comprises:

(i) Performing an at least indirect and preferably direct optical detection of at least one part of the dental treatment means during the dental treatment using an optical detection device or performing an optical recording (detection) of the dental treatment means during the dental treatment using an optical detection device. Herein, it is preferably conceivable that, in the case of an indirect recording of the dental treatment means, a position and/or orientation and/or alignment of the hand, which is guiding the dental treatment means, is recorded. An indirect recording of the dental treatment means preferably describes the real (actual) optical recording of the dental treatment means.

(ii) Generating image data representing the optical recording, wherein the image data preferably comprises or represents several grades of deformation of the dental treatment means. Preferably a bending and/or torsion of a toothbrush shaft and/or of a toothbrush head is recorded as a deformation. However it is additionally or alternatively also conceivable that a deformation of the bristles of a toothbrush is recorded or determined.

(iii) Analyzing the image data to determine the particular degree of deformation of the dental treatment means.

(iv) Determining the pressure, wherein the pressure is determined at least in accordance with the deformation of the dental treatment means and in accordance with further dental treatment means data, wherein the dental treatment means data comprises data concerning properties of the dental treatment means.

Furthermore, a signal or information may be output via an output device in accordance with the determined pressure. Preferably the signal or the information represents a guidance for the user of the dental treatment means, such as for the person undergoing the dental treatment. The recording (detection) of the pressure or the output of the signals to be output in accordance with the detected pressure preferably takes place in real time.

The signals and/or information are, particular preferably, output using an optical outputting device. The optical outputting device is preferably a component of a device to which also the optical detection device belongs. The signals and/or information with respect to the pressure are particular preferably simultaneously and/or using the same outputting device communicated to the same person, which is also used to communicate correction parameters for adapting the dental treatment movements of a person, such as the person who is undergoing and/or performing the dental treatment.

The data concerning the properties of the dental treatment means can include material properties and/or strength values and/or dimensions and/or bending stiffness and/or brand and/or age and/or number of usage, such as duration of usage, etc.

According to a further embodiment of the present teachings, an object is optically recorded (captured) such that at least the extension of the object in one dimension, i.e. the length and/or width and/or height and/or circumference, is known, and the extension(s) of the object in the known dimension(s) is (are) used for the determination of dimension parameters in order to detect geometric relationships, like e.g. the length of the path traveled by the dental treatment means during the dental treatment and/or the dimensions of the teeth, such as of the visible parts of the teeth and/or the dimensions of the dental treatment means and/or the distance of the teeth and/or the dental treatment means with respect to the detection device, etc. Herein, the object is preferably the person using the dental treatment means, wherein the known dimension of the person preferably is his/her height. It is additionally or alternatively conceivable that the object is the dental treatment means, such as the toothbrush, wherein the known dimension(s) of the toothbrush is (are) preferably the length and/or width and/or height and/or circumference.

Furthermore, the present teachings also relate to a system or a method comprising:

at least an optical detection device, such as at least one camera, for recording (capturing) of data with respect to at least one motion parameter, such as the movement direction, the acceleration, the travelled path and/or the velocity, of a dental treatment means and a data processing device for separation of an image part representing the dental treatment means from at least one other image part recorded by the optical detection device and for determining at least one movement pattern corresponding to the motion parameter using the separated image part, wherein the optical detection device comprises preferably at least one camera, such as exactly or at least two cameras, for the preferably three-dimensional recording (capturing) of the at least one motion parameter of a dental treatment means, wherein the processor device preferably defines a three-dimensional coordinate system moving together in space with the hand guiding the dental treatment means during movement of the dental treatment means, wherein the optical detection device preferably records a part (portion) of the head of a person and defines a three-dimensional coordinate system on the recorded part of the head, wherein movement of the dental treatment means is preferably determined in accordance with the defined coordinate system of the head or wherein movement of the recorded part (portion) of the head is determined in accordance with the coordinate system of the dental treatment means, wherein the processor device is preferably a mobile phone or a tablet PC and sends the recorded data preferably via the internet to a server device for further processing and/or receives via internet data for outputting by an outputting device of the mobile phone or the tablet PC, and wherein the data preferably comprise information concerning motion parameters of the dental treatment means and/or of the pressure, with which the dental treatment means is pressed against the teeth and/or the gum.

A database is preferably provided that comprises dental-treatment-means-data. Herein, it is conceivable that the database is provided locally on the end-user device and/or on a server. An identification means, such as a software based identification means, is preferably provided. The identification means records (captures), e.g. optically captures, the dental treatment means or information that represents the dental treatment means, like e.g. a QR-code. The optically recorded (captured) dental treatment means is preferably represented by image information or image data, which are preferably correlated with image information or image data with respect to a plurality of dental treatment means provided in said database. Data or information concerning the properties of the individual dental treatment means are preferably stored in the database. In case of a match of the data or information contained in the database with the recorded image data or image information, preferably a selection and utilization of the data or information stored in the database with respect to the specific or identified dental treatment means takes place to determine the pressure.

A link with the data or information, which are provided in the database, associated with a dental treatment means is further possible using a linkage, like e.g. by reading out a code, such as an optical code, like e.g. a bar code or QR-code. Furthermore, it is additionally or alternatively conceivable that a screen (user interface) for manually inputting of the dental-treatment-means-data or—properties is provided and the manually inputted data or information are used for determining the pressure. Additionally or alternatively, it is conceivable that the data or information concerning the dental treatment means are transferred into the database using a radio device, like e.g. a near-field-communication (NFC) or Bluetooth, or a linkage to the database is generated or the data for determining the pressure are stored.

The present teachings further relate to a computer program product for executing of one or multiple above- or below-described methods and/or for statistical analysis of the generated datasets.

The terms "optical detection device" and "optical capturing device" can be understood as being synonymous in the context of the present disclosure.

Further benefits, goals and features of the present teachings will be understood upon reading the following description of the attached figures, in which exemplary features according to the present teachings, such as processor devices or systems for recording the movement patterns during a dental treatment, are illustrated. Components of the devices and methods according to the present teaching, which match at least substantially with respect to their function can be marked with the same reference symbol, wherein such components do not have to be marked or described in all figures.

BRIEF DESCRIPTION OF THE DRAWINGS

In the following, embodiments of the invention are described in an exemplarily manner with reference to the attached figures.

DETAILED DESCRIPTION OF THE INVENTION

Figure 1A:
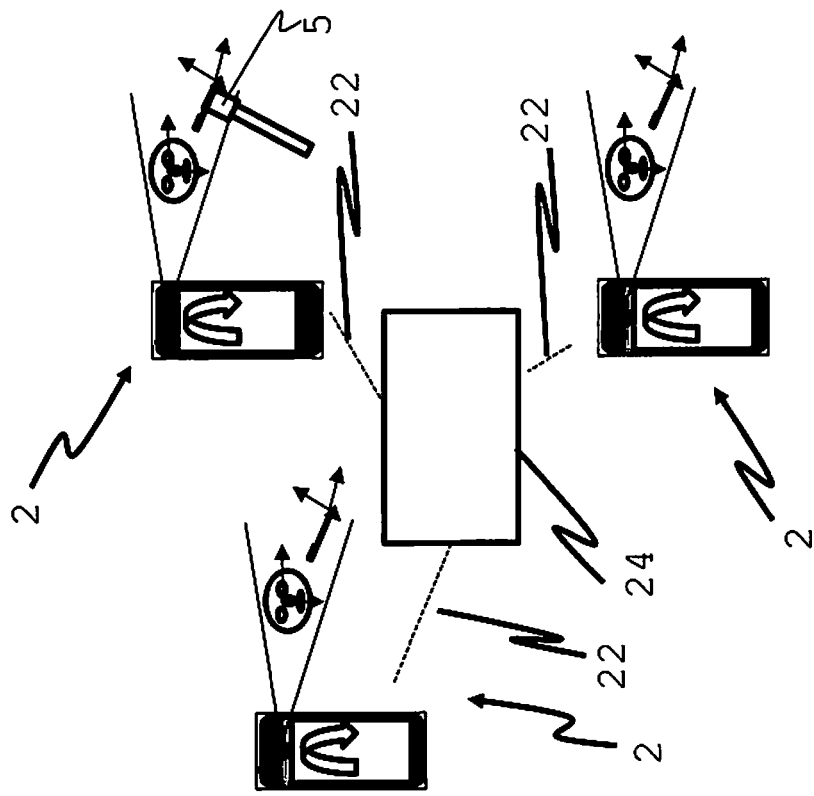
FIG. 1A shows one embodiment of a system according to the present teachings for recording (capturing) dental treatment movements.

In FIG. 1A, a system 1 for recording (capturing) dental treatment movements using a processor device 2 or a mobile end-user device 2 is shown. The mobile end-user device 2, which is preferably configured as a mobile phone, herein preferably has at least or exactly one optical detection device 4, such as an optical capturing device 4, that can be preferably formed as a camera. The camera preferably records (captures) exactly or more than 15 fps (frames per second), exactly, up to or more than 30 fps, exactly, up to or more than 45 fps, exactly, up to or more than 60 fps, exactly, up to or more than 75 fps, exactly, up to or more than 90 fps, exactly, up to or more than 120 fps or exactly, up to or more than 200 fps.

Reference number 6 denotes the recording (detection) area, in which preferably at least one part (portion) of the head, such as one or both pupils, the nose and/or the mouth, of a person 8 as well as at least one part (portion) of the hand 5 guiding the dental treatment means 14 are present. Reference numbers 10 and 12 denote preferably person-fixed axes or coordinate directions, which follow a movement of the head preferably exactly. Reference number 14 denotes a dental treatment means that is formed as toothbrush, which is moved in space according to reference number 16 and is thus moved relative to the head.

Motion sequences for correcting the movement and/or for specifying a motion sequence are displayable on the optical outputting device (display, screen) 18 of the processor device 2.

Figure 1B:
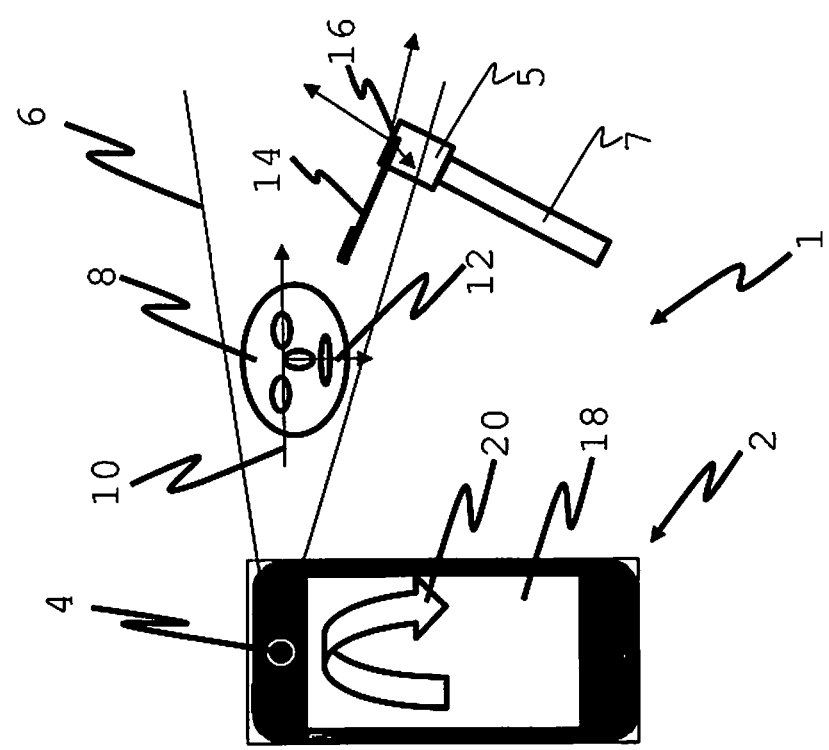
FIG. 1B shows an internet based network according to the present teachings, in which multiple systems are involved.

FIG. 1B shows that multiple processor devices 2 transmit via a data link, such as an internet link, data to a server that preferably generates optimized movement characteristics, such as in accordance with medical condition histories or defect histories of the individual persons.

Both FIGS. 1A and 1B underlie a method according to the present teachings for determining a movement pattern of a dental treatment means, such as a toothbrush, during a dental treatment, such as a teeth cleaning. Such as method preferably comprises the following steps 1 and 2:

1. Moving the dental treatment means to treat surface parts of the teeth in at least an X-/Y-plane, wherein data concerning at least one motion parameter (e.g., the movement direction or—rotation, the acceleration, the path and/or the velocity) of the dental treatment means 14 relative to a reference system 10 that moves with the head 8 of the treated person are recorded (detected) by the at least one optical detection device 4. The data preferably consist of image information, like e.g. an arrangement of pixels, and preferably describe (represent) at least one part (portion) of the head 8 of the person and at least one part of the hand 5 of the person, with which the person is guiding the dental treatment means. Reference number 7 denotes the arm of the person from which the hand 5 guiding the dental treatment means 14 extends.

The processor device 2 defines a further three-dimensional reference system 16, that moves in space together with the dental treatment means 14 during a movement of the dental treatment means 14, wherein the further reference system 16 is particular preferably defined by characteristic anthropometric body points of the hand, body lines of the hand and/or body surfaces of the hand, with which the dental treatment means 14 is guided.

This further three-dimensional reference system 16 defined by hand parts/points/features is beneficial since the dental treatment means 14 is typically partially or even completely enclosed by the hand 5 of the user and thus can be at least partially invisible (hidden) for the optical detection device 4. Based on the movement of the hand characteristic(s), such as anthropometric, body points of the hand, body lines of the hand and/or body surfaces of the hand defining the further reference system 16, the position and/or orientation of the dental treatment means 14 is determinable. The processor device 2 preferably analyzes data, such as image information, recorded (captured) by the optical detection device 4 to define the further three-dimensional reference system 16.

However, it is also conceivable that the data recorded by the optical detection device 4 are processed or analyzed by a processor device 2, which is located outside the mobile end-user device. Herein, the processor device may be a server device that receives the data via an internet connection. The processor device configured as a server device preferably sends the processed or modified or analyzed data or data based thereon via an internet connection to the end-user device.

2. Providing the recorded (captured) data to the processor device or to a further processor device for the determination of the movement pattern as well as preferably the determination of the movement pattern using the processor device or using the further processor device. Herein, it is conceivable the further reference system is defined e.g. using a processor device of a mobile or stationary end-user device. Data recorded by the optical detection device 4 with respect to the reference system 10 moving with the head 8 of the person and with the respect to the reference system 16 moving with the hand 5 of the person is preferably analyzed. Particular preferably the relative movements of the reference systems 10, 16 are determined with respect to each other.

Furthermore, the orientation and/or position of the dental treatment means 14, such as of the bristle part of the toothbrush, is determined with respect to the hand 5 guiding the dental treatment means 14 preferably at least temporarily, such as before and/or during tooth brushing. The determination of the position and/or orientation of the dental treatment means 14, such as of the bristle part of the toothbrush, preferably takes place by analyzing the data determined by the optical detection device 4.

Figures 2A, 2B:
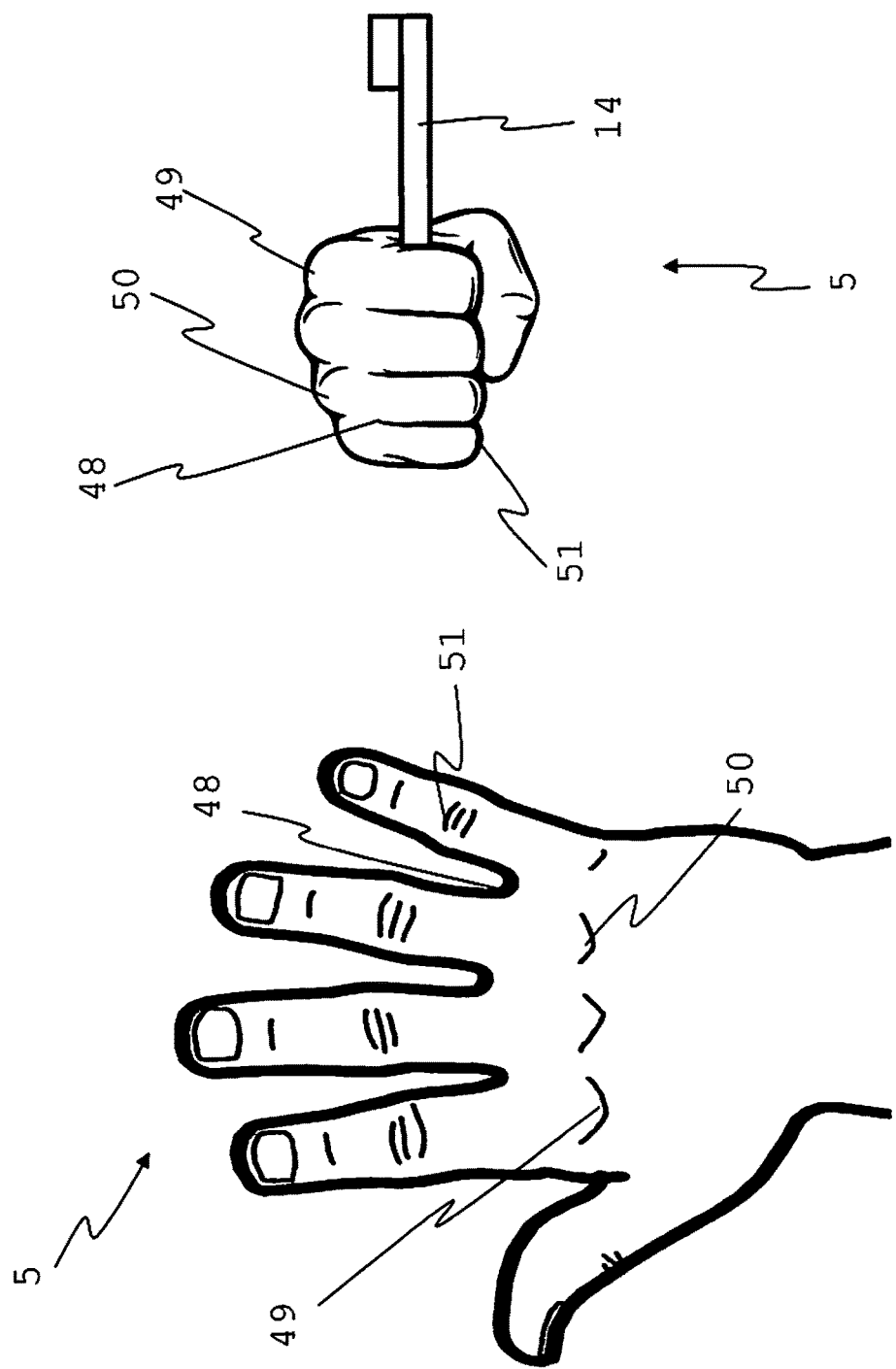
FIG. 2A shows an outstretched hand with characteristic surface points or surface parts.
FIG. 2B shows a hand clenched into a first with characteristic surface points or surface parts, wherein the hand is holding a dental treatment means (toothbrush).

FIG. 2A shows the back of the hand 5, wherein reference numbers 48, 49, 50 and 51 denote purely exemplary characteristic points on the surface of the hand. Thus, reference number 48 denotes the transition between two fingers. Reference numbers 49 and 50 denote the knuckles of the hand and reference number 51 denotes a knuckle of a finger. It has been recognized that these body surface points or—parts and similar body surface points or—parts are always very characteristic and are therefore very suitable for an optical recording (detection), whereby the present teachings facilitate a very simple and functionally very reliable method for a user.

In FIG. 2B the hand 5 is shown in a purely exemplary manner together with a dental treatment means 14. This illustration shows individual characteristic body points or—sections, as they are preferably recorded (detected) by the optical detection device 4.

The invention claimed is:

1. An electric toothbrush comprising:
   a brush head for contacting a tooth surface,
   a handle for holding the toothbrush, the brush head being disposed at an end of the handle,
   an acceleration sensor configured to sense acceleration of the electric toothbrush while the electric toothbrush is moving at least in an X-/Y-plane to treat surface parts of the teeth of a person and to generate motion sensor data, wherein the acceleration sensor is provided inside the electric toothbrush,
   a pressure sensor configured to detect a contact pressure between the brush head and the teeth and to generate contact pressure data, wherein the pressure sensor is provided inside the electric toothbrush,
   a wireless communication interface configured to wirelessly transmit the motion sensor data in real-time and the contact pressure data in real-time to a mobile phone or tablet PC, at least one first outputting device configured to visually output signals or commands in accordance with the detected contact pressure, and at least one second outputting device configured to haptically output signals or commands in accordance with the detected contact pressure and to generate vibrations that represent the output signals or commands.

2. The electric toothbrush according to claim 1, wherein the wireless communication interface is configured to receive treatment mode data for operating the electric toothbrush in one treatment mode selected from a plurality of treatment modes.

3. The electric toothbrush according to claim 2, wherein the wireless communication interface is configured to transmit the motion sensor data and contact pressure data in a processed state to the mobile phone or tablet PC.

4. A system comprising:
the electric toothbrush according to claim 2, and
a mobile phone or tablet PC configured to be connectable, at least temporarily, with the internet,
wherein the mobile phone or tablet PC includes a processor configured to process the motion sensor data and contact pressure data to generate correction information and to display the correction information.

5. The system according to claim 4, wherein the mobile phone or tablet PC comprises a screen configured to:
display the correction information and the plurality of treatment modes, and
enable a user to select one treatment mode from the plurality of treatment modes displayed on the screen.

6. The system according to claim 5, wherein the mobile phone or tablet PC is configured to receive data via the internet for outputting to the screen.

7. The system according to claim 6, wherein the mobile phone or tablet PC stores data representing information with respect to at least one property of the electric toothbrush.

8. The system according to claim 7, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data, and
the processor of the mobile phone or the tablet PC is configured to generate the correction information based on the motion sensor data and the image data.

9. The system according to claim 4, wherein the mobile phone or tablet PC is configured to:
send the motion sensor data and contact pressure data via the internet to a server for further processing, and
receive data via the internet for outputting to the screen.

10. The system according to claim 9, wherein the mobile phone or tablet PC stores data representing information with respect to at least one property of the electric toothbrush.

11. The system according to claim 4, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data,
the processor of the mobile phone or the tablet PC is configured to:
identify the at least one body part of the person in the image data,
separate toothbrush image data from said image data and
generate the correction information based on the motion sensor data and the separated toothbrush image data, and
a screen of the mobile phone or tablet PC is configured to display the correction information.

12. The system according to claim 4, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data,
the processor of the mobile phone or the tablet PC is configured to generate the correction information based on the motion sensor data and the image data, and
a screen of the mobile phone or tablet PC is configured to display the correction information.

13. A system comprising:
the electric toothbrush according to claim 2, and
a non-transitory computer storage medium comprising computer-readable instructions that, when executed, process the motion sensor data and contact pressure data to generate correction information and display the correction information on the screen of a mobile phone/tablet PC.

14. The system according to claim 13, wherein the computer-readable instructions include instructions that, when executed, display a plurality of treatment modes for operating the electric toothbrush on the screen and send instructions for operating the electric toothbrush according to a selected one of the treatment modes to the wireless communication interface.

15. The system according to claim 14, wherein the computer-readable instructions further include instructions that, when executed, process data received via the internet to be output on the screen and process the motion sensor data and contact pressure data to send the motion sensor data and contact pressure data via the internet to a server for further processing.

16. The system according to claim 15, wherein the computer-readable instructions further include instructions that, when executed, process property data stored in the mobile phone/tablet PC, wherein the property data represents at least one property of the electric toothbrush.

17. The system according to claim 16, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data,
a processor of the mobile phone or the tablet PC is configured to generate the correction information based on the motion sensor data and the image data, and
a screen of the mobile phone or tablet PC is configured to display the correction information.

18. The system according to claim 13, wherein the computer-readable instructions further include instructions that, when executed, process property data stored in the mobile phone/tablet PC, wherein the property data represents at least one property of the electric toothbrush.

19. The system according to claim 13, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data, and
a processor of the mobile phone or the tablet PC is configured to generate the correction information based on the motion sensor data and the image data.

20. A system comprising:
the electric toothbrush according to claim 2,
a non-transitory computer storage medium comprising computer-readable instructions that, when executed, obtain preprocessed data from the electric toothbrush and transmit processed data from a mobile phone or tablet PC to a server, and
the server comprising computer-readable instructions that, when executed, process, modify or analyze the preprocessed data and transmit data back to the mobile phone or tablet PC.

21. The system according to claim 20, wherein the computer-readable instructions comprise instructions that, when executed, display a plurality of treatment modes for operating the electric toothbrush on the screen and send instructions for operating the electric toothbrush according to a selected one of the treatment modes to the wireless communication interface.

22. The system according to claim 21, wherein:
the computer-readable instructions comprise instructions that, when executed, process data received via the internet to be output on the screen and processing the motion sensor data and contact pressure data to send the motion sensor data and contact pressure data via the internet to a server for further processing, and
the computer-readable instructions comprise instructions that, when executed process property data stored in the mobile phone/tablet PC, wherein the property data represents at least one property of the electric toothbrush.

23. The system according to claim 22, wherein:
the computer-readable instructions comprise instructions that, when executed, process data received via the internet to be output on the screen and processing the motion sensor data and contact pressure data to send the motion sensor data and contact pressure data via the internet to a server for further processing, and
the computer-readable instructions comprise instructions that, when executed process property data stored in the mobile phone/tablet PC, wherein the property data represents at least one property of the electric toothbrush.

24. The system according to claim 23, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data,
a processor of the mobile phone or the tablet PC is configured to generate the correction information based on the motion sensor data and the image data, and
a screen of the mobile phone or tablet PC is configured to display the correction information.

25. The system according to claim 20, wherein:
a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data,
a processor of the mobile phone or the tablet PC is configured to generate the correction information based on the motion sensor data and the image data, and
a screen of the mobile phone or tablet PC is configured to display the correction information.

26. A method for operating the electric toothbrush according to claim 2, the method comprising:
generating motion data using the acceleration sensor of the electric toothbrush,
generating contact pressure data using the pressure sensor of the electric toothbrush,
transmitting generated motion data in real-time and generated contact pressure data in real-time to the mobile phone or tablet PC,
visually outputting signals or commands on the mobile phone or tablet PC in accordance with the generated contact pressure data,
receiving treatment mode data for operating the electric toothbrush in one treatment mode selected from a plurality of treatment modes,
visually outputting signals or commands in accordance with the generated contact pressure data using a first outputting device of the electric toothbrush, and
haptically outputting signals or commands in accordance with the generated contact pressure data using a second outputting device of the electric toothbrush.

27. The method according to claim 26, wherein:
the mobile phone or a tablet PC includes a processing device configured to be connectable, at least temporarily, with the internet,
the processing device includes a processor configured to process the motion sensor data and contact pressure data to generate correction information and to display the correction information,
the processing device comprises a screen configured to display the correction information and the plurality of treatment modes, and to enable a user to select one treatment mode from the plurality of treatment modes displayed on the screen,
the processing device is configured to receive data via the internet to be output to the screen, and
the method further comprises:
connecting the mobile phone or the tablet PC with the internet,
processing the motion sensor data and contact pressure data,
generating the correction information,
displaying the correction information on the screen,
selecting one treatment mode from the plurality of treatment modes displayed on the screen,
receiving data via the internet,
outputting the data received via the internet to the screen,
generating movement pattern data based at least in part on the recorded motion data, and
assigning the movement pattern data to a specific phone number or email address.

28. The method according to claim 26, further comprising:

using a camera of the mobile phone or tablet PC to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data, using a processor of the mobile phone or the tablet PC to identify the at least one body part of the person in said image data, using the processor of the mobile phone or the tablet PC to separate toothbrush image data from said image data, and determining correction parameters for adapting the movement of the toothbrush based on the motion sensor data and the separated toothbrush image data and displaying the correction information on a screen of the mobile phone or tablet PC.

29. The method according to claim 26, further comprising:

using a camera of the mobile phone or tablet PC to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data, determining correction parameters for adapting the movement of the toothbrush based on the motion sensor data and the image data, and displaying the correction information on a screen of the mobile phone or tablet PC.

30. An electric toothbrush comprising:

a brush head for contacting a tooth surface, a handle for holding the toothbrush, the brush head being disposed at an end of the handle, an acceleration sensor configured to sense acceleration of the electric toothbrush while the electric toothbrush is moving at least in an X-/Y-plane to treat surface parts of the teeth of a person and to generate motion sensor data, wherein the acceleration sensor is provided inside the electric toothbrush, a pressure sensor configured to detect a contact pressure between the brush head and the teeth and to generate contact pressure data, wherein the pressure sensor is provided inside the electric toothbrush, a wireless communication interface configured to wirelessly transmit the motion sensor data in real-time and the contact pressure data in real-time to a mobile phone or tablet PC, the wireless communication interface being configured to receive treatment mode data for operating the electric toothbrush in one treatment mode selected from a plurality of treatment modes, and at least one outputting device configured to visually output signals or commands in accordance with the detected contact pressure, or at least one outputting device configured to haptically output signals or commands in accordance with the detected contact pressure and to generate vibrations that represent the output signals or commands.

31. A system comprising:

the electric toothbrush according to claim 30, and a non-transitory computer storage medium comprising computer-readable instructions that when executed, process the motion sensor data and contact pressure data to generate correction information and display the correction information on a screen of the mobile phone or the tablet PC, wherein:

a camera of the mobile phone or tablet PC is configured to capture an image area containing (i) at least one body part selected from one or both pupils, the nose, eyebrows, eye hole, lips, ears, cheeks and/or chin of the person, as well as (ii) the toothbrush moving at least in an X-/Y plane to treat surface parts of teeth of the person, thereby generating image data, and a processor of the mobile phone or the tablet PC is configured to generate correction information based on the motion sensor data and the image data.

* * * * *